(12) United States Patent
Miculka et al.

(10) Patent No.: US 8,268,813 B2
(45) Date of Patent: Sep. 18, 2012

(54) ZILPATEROL ENANTIOMER COMPOSITIONS AND METHODS OF MAKING AND USING SUCH COMPOSITIONS

(75) Inventors: Christian Miculka, Wiesbaden (DE); Thorsten Meyer, Schwabenheim (DE); Christopher Kern, Schwabenheim (DE); Serge Francois Droux, Romainville (FR)

(73) Assignee: Intervet International B.V., Boxmeer (NL)

( * ) Notice: Subject to any disclaimer, the term of this patent is extended or adjusted under 35 U.S.C. 154(b) by 438 days.

(21) Appl. No.: 12/373,221

(22) PCT Filed: Jul. 10, 2007

(86) PCT No.: PCT/EP2007/057036
§ 371 (c)(1),
(2), (4) Date: Oct. 8, 2009

(87) PCT Pub. No.: WO2008/006828
PCT Pub. Date: Jan. 17, 2008

(65) Prior Publication Data
US 2010/0022490 A1 Jan. 28, 2010

Related U.S. Application Data

(60) Provisional application No. 60/819,954, filed on Jul. 10, 2006.

(51) Int. Cl.
*A61P 1/16* (2006.01)
*A61K 31/551* (2006.01)
*A23K 1/16* (2006.01)
*C07D 487/06* (2006.01)

(52) U.S. Cl. .................................. 514/214.02; 540/579

(58) Field of Classification Search ............. 514/214.02; 540/579
See application file for complete search history.

(56) References Cited

U.S. PATENT DOCUMENTS

| | | |
|---|---|---|
| 4,900,735 A | 2/1990 | Grandadam |
| 2005/0284380 A1 | 12/2005 | Montgomery |

FOREIGN PATENT DOCUMENTS

WO 2006108424 10/2006

OTHER PUBLICATIONS

B. Bocca, et al., Journal of Separation Science, 26:5 pp. 363-368 (Apr. 2003).

*Primary Examiner* — Brenda Coleman
(74) *Attorney, Agent, or Firm* — TraskBritt

(57) ABSTRACT

This invention is directed generally to zilpaterol enantiomer compositions, and, in particular, to compositions comprising the 6R,7R zilpaterol enantiomer. This invention is also directed to processes for making such compositions; methods for using such compositions to, for example, increase the rate of weight gain, improve feed efficiency, and/or increase carcass leanness in livestock, poultry, and/or fish; and uses of such compositions to make medicaments. This invention is further directed to methods for determining the absolute configurations of zilpaterol enantiomers.

28 Claims, No Drawings

ZILPATEROL ENANTIOMER COMPOSITIONS AND METHODS OF MAKING AND USING SUCH COMPOSITIONS

PRIORITY CLAIM TO RELATED PATENT APPLICATIONS

This patent claims priority under 35 U.S.C. §371 as a national phase of International Patent Application No. PCT/EP2007/057036 (filed Jul. 10, 2007; and published on Jan. 17, 2008, as International Publication No. WO 2008/006828), which, in turn, claims priority to U.S. Application No. 60/819,954 (filed Jul. 10, 2006). The entire text of each of the above-referenced patent applications is hereby incorporated by referenced into this patent.

CROSS-REFERENCE TO RELATED PATENT APPLICATIONS

This patent claims priority to U.S. Provisional Patent Application No. 60/819,954 (filed Jul. 10, 2006). The entire text of that patent application is incorporated by reference into this patent.

FIELD OF THE INVENTION

This invention is directed generally to zilpaterol enantiomer compositions, and, in particular, to compositions comprising the 6R,7R zilpaterol enantiomer. This invention is also directed to processes for making such compositions; methods for using such compositions to, for example, increase the rate of weight gain, improve feed efficiency, and/or increase carcass leanness in livestock, poultry, and/or fish; and uses of such compositions to make medicaments. This invention is further directed to methods for determining the absolute configurations of zilpaterol enantiomers.

BACKGROUND OF THE INVENTION

Zilpaterol is a known adrenergic β-2 agonist having the following structure:

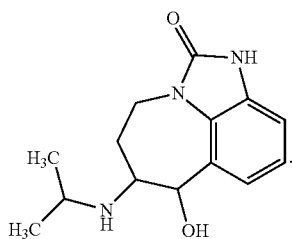

The IUPAC name for zilpaterol is 4,5,6,7-tetrahydro-7-hydroxy-6-(isopropylamino)imidazo[4,5,1-jk]-[1]benzazepin-2(1H)-one. The Chemical Abstracts name for zilpaterol is 4,5,6,7-tetrahydro-7-hydroxy-6-[(1-methyl-ethyl) amino]-imidazo [4,5,1-jk][1]benzazepin-2(1H)-one.

Zilpaterol has two chiral carbons:

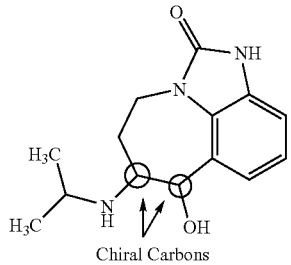

Chiral Carbons

Consequently, zilpaterol has four optical enantiomers. These enantiomers are identified as "(6R,7R)," "(6R,7S)," "(6S,7R)," and "(6S,7S)." CAS No. 119520-05-7 corresponds to racemic trans zilpaterol (i.e., a mixture of the (6R,7R) and (6S,7S) enantiomers), and has been identified in the literature as "RU42173." The trans enantiomers have the following structures:

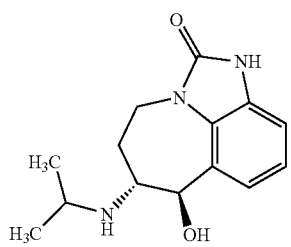

(6R,7R)

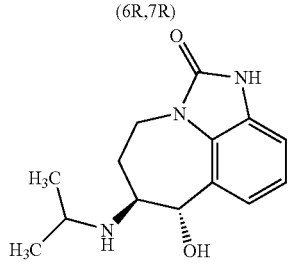

(6S,7S)

Zilpaterol is well known in the art.

For example, in U.S. Pat. No. 4,585,770, Fréchet et al. discuss compounds encompassed by a genus characterized as 6-amino-7-hydroxy-4,5,6,7-tetrahydro-imidazo[4,5,1-j-k] [1]-benzazepin-2-(1H)-one derivatives, and, in particular, derivatives (and pharmaceutically acceptable acid addition salts thereof) corresponding to the following structure:

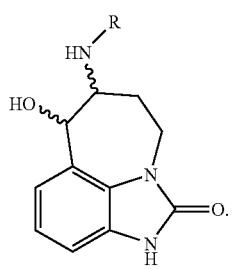

Here, R can be various substituents, and the wavy lines indicate that the bonds to the 6-amino and 7-OH groups have the trans configuration. This genus encompasses racemic trans zilpaterol when R is isopropyl. Fréchet et al. state that such compounds may be used as an active ingredient for inducing antihypertensive and hypotensive activity in a warm-blooded animal.

In U.S. Pat. No. 4,900,735, Grandadam discusses a zootechnical composition comprising at least one compound of the following formula or a pharmaceutically acceptable acid addition salt thereof:

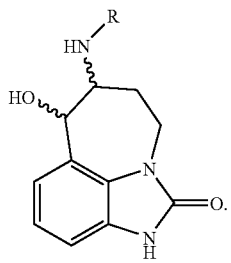

Here, R can be various substituents, and the wavy lines indicate that the bonds to the 6-amino and 7-OH groups have the trans configuration. As with the genus discussed in U.S. Pat. No. 4,585,770, this genus encompasses racemic trans zilpaterol when R is isopropyl. Grandadam states that such a composition may be used to increase the weight of cattle, pigs, or poultry, and may optionally further comprise a steroid.

In U.S. Pat. Nos. 5,731,028 and 5,847,124, Chevremont et al. discuss crystallized anhydrous zilpaterol hydrochloride, and particularly crystallized anhydrous zilpaterol hydrochloride wherein less than 5% of the crystals have a size of less than 15 μm, and at least 95% of the crystals have a size of less than 250 μm. According to Chevremont et al., such crystals may be incorporated into animal feed to increase body weight and meat quality. Chevremont et al. provide methods for making such crystals, and discuss using the crystals to make animal premixes in which the crystals are secured to a corn cob support having a greater particle size. They also discuss monohydrate and trihydrate intermediates that can be useful in, for example, making the crystals.

In U.S. Pat. No. 7,207,289, Montgomery discusses methods for increasing beef production, reducing feed intake while maintaining beef production, and reducing incidences of liver abscess in cattle. These methods comprise administering a feed comprising an ionophore and macrolide antibiotic during an initial period, and then administering a feed comprising zilpaterol with essentially no ionophore or macrolide antibiotic.

There has been some discussion in the art relating to enantiomers of various adrenergic β-2 agonists. Such discussion may be found in, for example, U.S. Pat. No. 6,110,974; U.S. Patent Appl. Publ. 2005/0113456; and U.S. Patent Appl. Publ. 2002/0132830.

There still exists a need for alternative compositions and methods for increasing the rate of weight gain, improve feed efficiency, and/or increase carcass leanness in livestock, poultry, and/or fish. The following disclosure describes such compositions and methods.

SUMMARY OF THE INVENTION

This invention is related to compositions comprising a zilpaterol enantiomer, while containing less of at least one (and typically two or all three) of the other enantiomers. Such a method is particularly suitable to be used with livestock (e.g., bovine and swine), poultry, and/or fish.

Briefly, this invention is directed, in part, to a composition. The composition comprises an amount of a 6R,7R enantiomer corresponding in structure to Formula (IA) or a salt thereof:

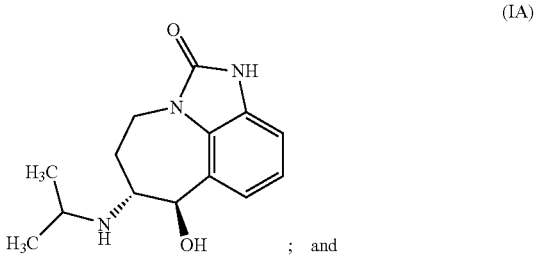

In some embodiments, the amount of the 6R,7R enantiomer or salt thereof in the composition is greater than any amount of any other enantiomer encompassed by Formula (I) or salt thereof:

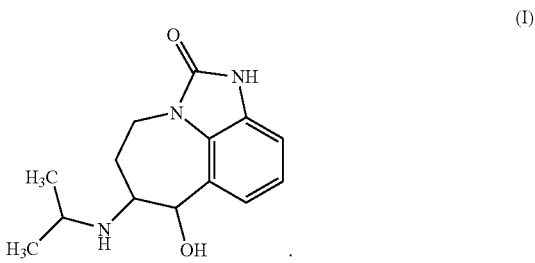

In other embodiments, the composition exhibits detectably less affinity for μ-opioid receptor binding in vitro than the composition would exhibit if the 6R,7R enantiomer were entirely replaced with racemic trans zilpaterol in an amount that equals twice the amount of the 6R,7R enantiomer.

This invention also is directed, in part, to a method of feeding an animal. This method comprises feeding an above-described composition to the animal.

This invention also is directed, in part, to methods for increasing an animal's rate of weight gain, improving an animal's feed efficiency, and/or increasing an animal's carcass leanness. These methods comprise administering an above-described composition to the animal.

This invention also is directed, in part, to a method of increasing beef production. This method comprises administering a first dosage regimen to a bovine animal for an initial period; and, at the end of the initial period, administering a second dosage regimen for from about 20 to about 40 days. The first dosage regimen comprises administering (e.g., feeding) an ionophore and an antibiotic in amounts that together constitute a therapeutically effective amount; and the second dosage regimen comprises administering (e.g., feeding) an above-described composition and essentially no ionophore or antibiotic.

This invention also is directed, in part, to a method of reducing feed intake of a bovine animal while maintaining beef production. This method comprises administering a first dosage regimen during a finishing period until from about 20 to about 40 days before the end of the finishing period; and during the about 20 to about 40 days before the end of the finishing period, administering a second dosage regimen. The first dosage regimen comprises administering (e.g., feeding) an ionophore and an antibiotic in amounts that together constitute a therapeutically effective amount. The second dosage regimen comprises administering (e.g., feeding) an above-described composition that comprises essentially no β-2 agonist other than the enantiomer, and essentially no ionophore or antibiotic.

This invention also is directed, in part, to a method of finishing a bovine animal. This method comprises administering a first dosage regimen during a finishing period until from about 20 to about 40 days before the end of the finishing period; and during the about 20 to about 40 days before the end of the finishing period, administering a second dosage regimen. The first dosage regimen comprises administering (e.g., feeding) an ionophore and an antibiotic in amounts that together constitute a therapeutically effective amount. The second dosage regimen comprises administering (e.g., feeding) an above-described composition that comprises essentially no β-2 agonist other than the enantiomer, and essentially no ionophore or antibiotic. This finishing method reduces the risk of a liver abscess in the bovine animal compared to the risk to a similar bovine animal that receives the first dosage regimen throughout the entire finishing period.

This invention also is directed, in part, to use of an above-described composition to make a medicament. Potential uses for such a medicament include increasing an animal's rate of weight gain, improving an animal's feed efficiency, and/or increasing an animal's carcass leanness.

This invention also is directed, in part, to a method for separating enantiomers of Formula (I) or salts thereof. The method comprises forming protected derivatives, and, in particular, benzyl carbamate derivatives, of the enantiomers.

This invention also is directed, in part, to a method for determining the absolute configuration of an enantiomer corresponding in structure to Formula (I) or a salt thereof. The method comprises reacting the enantiomer with 2,4'-dibromoacetophenone to form a 4-bromophenylacyl derivative of the enantiomer.

Further benefits of Applicants' invention will be apparent to one skilled in the art from reading this specification.

DETAILED DESCRIPTION OF PREFERRED EMBODIMENTS

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this specification, and may be variously modified.

The compositions of this invention comprise the trans enantiomer of Formula (I) (or a salt thereof) that has a negative optical rotation, as measured by a polarimeter:

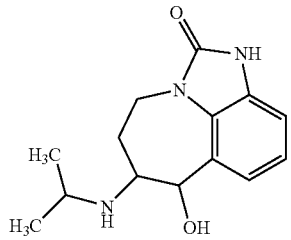

This enantiomer is sometimes identified in this specification as the "negative trans enantiomer." When using an HPLC column to separate the enantiomers in racemic trans zilpaterol under the conditions set forth in Examples 1 and 2 below, this enantiomer emerges from the column after the enantiomer having the positive optical rotation (i.e., the "positive trans enantiomer"). Applicants have determined that the negative trans enantiomer is the 6R,7R enantiomer, and that the positive trans enantiomer is the 6S,7S enantiomer.

The ratio of the amount of the 6R,7R enantiomer to the 6S,7S enantiomer in the compositions of this invention is greater than 1:1. Preferably, the compositions are substantially free of the 6S,7S enantiomer, i.e., the ratio of the amount of the 6R,7R enantiomer to the amount of the 6S,7S enantiomer is greater than about 70:30. In some such embodiments, the ratio is greater than about 85:15, greater than about 90:10, greater than about 95:5, greater than about 98:2, greater than about 99:1, or greater than about 99.5:0.5.

In general, the ratio of the amount of the 6R,7R enantiomer to the total amount of all the other enantiomers of Formula (I) combined (i.e., the total amount of the 6S,7S enantiomer and the two cis enantiomers) in the compositions of this invention is greater than 1:1. In some such embodiments, the compositions are substantially free of all the other enantiomers, i.e., the ratio of the amount of the 6R,7R enantiomer to the total amount of all the other enantiomers combined is greater than about 70:30. In some such embodiments, the ratio is greater than about 85:15, greater than about 90:10, greater than about 95:5, greater than about 98:2, greater than about 99:1, or greater than about 99.5:0.5.

In some embodiments, the concentration of the 6R,7R enantiomer in the compositions of this invention is greater than about 50% (by weight). In some such embodiments, the concentration is greater than about 70% (by weight), greater than about 85% (by weight), greater than about 90% (by weight), greater than about 95% (by weight), greater than about 98% (by weight), greater than about 99% (by weight), or greater than about 99.5% (by weight).

The concentration of the 6S,7S enantiomer in the compositions of this invention is less than 50%. In some embodiments, the concentration of the 6S,7S enantiomer is less than about 30% (by weight), less than about 15% (by weight), less than about 10% (by weight), less than about 5% (by weight), less than about 2% (by weight), less than about 1% (by weight), or less than about 0.5% (by weight). In some such embodiments, the total concentration of the 6S,7S enantiomer and the two cis enantiomers combined is less than 50%. For example, in some embodiments, the total concentration of these enantiomers is less than about 30% (by weight), less than about 15% (by weight), less than about 10% (by weight), less than about 5% (by weight), less than about 2% (by weight), less than about 1% (by weight), or less than about 0.5% (by weight).

A salt of the 6R,7R enantiomer may be advantageous over the free base due to one or more of the salt's physical properties, such as pharmaceutical stability in differing temperatures and humidities; crystalline properties; and/or a desirable solubility in water, oil, or other solvent. In some instances, a salt may be used as an aid in the isolation, purification, and/or resolution of the enantiomer. Salts can typically be formed by, for example, mixing the free base with an acid using various known methods in the art. To the extent a salt of the 6R,7R enantiomer is intended to be administered in vivo (i.e., to an animal) for a therapeutic benefit, the salt preferably is pharmaceutically acceptable. The term "pharmaceutically acceptable" is used adjectivally to mean that the modified noun is appropriate for use in a pharmaceutical product. When it is used, for example, to describe a salt or excipient, it characterizes the salt or excipient as being compatible with the other ingredients of the composition, and not deleterious to the intended recipient animal to the extent that the deleterious effect(s) outweighs its benefit(s).

Suitable salts generally include acid addition salts. In general, an acid addition salt can be prepared by reacting the enantiomer free base with an approximately stoichiometric amount of an inorganic or organic acid. Examples of often suitable inorganic acids for making pharmaceutically acceptable salts include hydrochloric, hydrobromic, hydroiodic, nitric, carbonic, sulfuric, and phosphoric acid. Examples of often suitable organic acids for making pharmaceutically acceptable salts generally include, for example, aliphatic, cycloaliphatic, aromatic, araliphatic, heterocyclic, carboxylic, and sulfonic classes of organic acids. Specific examples of often suitable organic acids include cholate, sorbate, laurate, acetate, trifluoroacetate (or "$CF_3COOH$" or "TFA"), formate, propionate, succinate, glycolate, gluconate, digluconate, lactate, malate, tartaric acid, citrate, ascorbate, glucuronate, maleate, fumarate, pyruvate, aspartate, glutamate, aryl carboxylic acid (e.g., benzoate), anthranilic acid, mesylate, stearate, salicylate, p-hydroxybenzoate, phenylacetate, mandelate, embonate (pamoate), alkylsulfonate (e.g., ethanesulfonate), arylsulfonate (e.g., benzenesulfonate), pantothenate, 2-hydroxyethanesulfonate, sulfanilate, cyclohexylaminosulfonate, $\beta$-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate. In some such embodiments, for example, the salt comprises a trifluoroacetate, mesylate, or tosylate salt. In other such embodiments, the salt comprises a hydrochloric acid salt.

The compositions of this invention may generally be used to increase the rate of weight gain, improve feed efficiency (i.e., decrease the amount of feed per amount of weight gain), and/or increase carcass leanness (i.e., increase protein content in carcass soft tissue) in livestock, poultry, and/or fish. Contemplated benefits of using the enantiomer compositions of this invention over racemic zilpaterol include, for example, greater efficacy, greater selectivity, improved handling characteristics, fewer side effects, lower drug tissue concentrations, and/or the ability to eliminate another enantiomer having adverse side effects.

It is particularly contemplated that the 6R,7R enantiomer compositions of this invention may be beneficial due to the lack of affinity of the 6R,7R enantiomer for the µ-opioid receptor. As shown below in Examples 4 and 5, the 6R,7R zilpaterol enantiomer appears to account for essentially all the $\beta_2$ agonist activity of racemic trans zilpaterol. And, as shown below in Example 6, Applicants have discovered that the 6R,7R zilpaterol enantiomer provides this activity while exhibiting comparatively less affinity toward the µ-opioid receptor. It is suggested in the art that less µ-opioid receptor affinity may generally coincide with various advantageous effects. See, e.g., Int'l Patent Appl. Publ. WO/2003/039469; Bodnar, *Peptides*, vol. 25, issue 4, pp. 697-725 (April 2004); Zhang et al., "Endogenous opioids and feeding behavior," *European Journal of Pharmacology*, vol. 545, Issues 2-3, pp. 147-152 (Sep. 18, 2006); Linn, et al., "Peripherally restricted µ-opioid receptor antagonists: a review," *Techniques in Regional Anesthesia and Pain Management*, vol. 11, issue 1, pp. 27-32 (January 2007); Salmi, et al., *European Journal of Pharmacology*, vol. 458, no. 1, pp. 101-106 (Jan. 1, 2003); and Colman, et al., "µ-1 opioid receptor stimulation decreases body temperature in conscious, unrestrained neonatal rats," *Society for Experimental Biol Med*, vol. 227(6), pp. 377-381 (2002) (these references are incorporated by reference into this patent). It is, therefore, contemplated that the 6R,7R enantiomer may provide one or more of such advantageous effects over racemic trans zilpaterol. Contemplated benefits include, for example, greater feed intake, which, in turn, results in greater body weight gain and/or a greater growth rate. Other contemplated benefits include, for example, greater gastrointestinal motility, greater lung ventilation, greater alertness, greater wakefulness, and/or undisturbed thermoregulation.

Typically, the compositions of this invention are administered orally. In some embodiments, the composition is added to the intended recipient animal's drinking water. In other embodiments, the enantiomer is added to the intended recipient's feed, either directly or as part of a premix. Suitable oral dosage forms for such embodiments include, for example, solid dosage forms (e.g., tablets, hard or soft capsules, granules, powders, etc.), pastes, and liquid dosage forms (e.g., solutions, suspensions, syrups, etc.). These dosage forms optionally comprise one or more suitable excipients. Such excipients generally include, for example, sweetening agents, flavoring agents, coloring agents, preservative agents, inert diluents (e.g., calcium carbonate, sodium carbonate, lactose, calcium phosphate, sodium phosphate, or kaolin), granulating and disintegrating agents (e.g., corn starch or alginic acid), binding agents (e.g., gelatin, acacia, or carboxymethyl cellulose), and lubricating agents (e.g., magnesium stearate, stearic acid, or talc). Liquid compositions will generally comprise a solvent. The solvent preferably has sufficient chemical properties and quantity to keep the enantiomer solubilized at temperatures at the normal storage temperature for the composition. In some instances, it may be desirable for the compositions to comprise one or more preservatives. The presence of a preservative may, for example, allow for the compositions to be stored over a greater amount of time.

In some embodiments, the zilpaterol enantiomer is in the form of particles adhered to a support, which, in turn, is fed to the intended recipient animal. The supported enantiomer may incorporated into the intended recipient's feed, either directly or as part of a premix. Contemplated supports include, for example, insert supports, such as calcium carbonate, limestone, oyster shell flour, talc, soybean hulls, soybean meal, soybean feed, soybean mill run, wheat middlings, rice hulls, corn meal, corn germ meal, corn gluten, starch, sucrose, and lactose. Particularly contemplated supports include corn cob supports, such as the support discussed in U.S. Pat. No. 5,731,028. In some embodiments employing a corn cob support, the size of the support is from about 300 to about 800 µm. Preferably, the zilpaterol enantiomer particles that are adhered to the support have a particle size that is less than the size of the support. Thus, for example, in some embodiments in which the support is from about 300 to about 800 µm, the enantiomer particles (or at least about 95% of the enantiomer particles) are less than about 250 µm. In some embodiments, the size of the majority of the enantiomer particles is from about 50 to about 200 µm. To avoid generating dust when making the supported enantiomer, it is preferred to avoid using extremely small enantiomer particles. In some embodiments, for example, the enantiomer particle size distribution is such that less than about 5% of the enantiomer particles have a particle size of less than about 15 µm. The methods discussed in, for example, U.S. Pat. No. 5,731,028 (inventors: Chevremont et al.; filed Jun. 6, 1996; issued Mar. 24, 1998; incorporated by reference into this patent) for making a specific size distribution of crystalline racemic trans zilpaterol may generally be applied when making crystals of the 6R,7R enantiomer having the above-described size distributions.

To the extent the composition is incorporated into feed, the feed mixture will vary depending on, for example, the type (e.g., species and breed), age, weight, activity, and condition of the intended recipient. For bovine and swine, various feeds are well known in the art, and often comprise cereals; sugars; grains; arachidic, tournsole, and soybean press cake; flours of animal origin, such as fish flour; amino acids; mineral salts; vitamins; antioxidants; etc. In general, the enantiomer composition can be incorporated into any feed that is available and used for the intended recipient animal.

It is contemplated that the compositions of this invention may be administered via non-oral routes, such as rectally, via inhalation (e.g., via a mist or aerosol), transdermally (e.g., via a transdermal patch), or parenterally (e.g., subcutaneous injection, intravenous injection, intramuscular injection, implanted device, partially implanted device etc.). In some particular embodiments, the compositions are administered via an implant, such as a subcutaneous implant. For administration to bovine or swine animals, for example, the composition may be administered in the form of an implant behind the ear or baleen.

In general, the compositions of this invention are administered in a dosage form that provides an effective amount of the 6R,7R enantiomer. This is particularly true where the enantiomer is the only active ingredient in the composition. To the extent the enantiomer is administered with another active ingredient(s), the dosage preferably comprises an amount of the enantiomer that, together with the amount of other active ingredient(s), constitutes an effective amount. In the context of the enantiomer, an "effective amount" is an amount sufficient to increase the rate of weight gain, improve feed efficiency, and/or increase carcass leanness in the intended recipient (typically livestock, poultry, and/or fish).

When the composition is orally administered, it is typically preferred to use a daily dosage form. The preferred total daily dose is typically greater than about 0.01 mg/kg (i.e., milligram of enantiomer per kilogram body weight), particularly for bovine and swine animals. In some such embodiments, the daily dose is from about 0.01 to about 50 mg/kg, from about 0.01 to about 10 mg/kg, from about 0.05 to about 2 mg/kg, from about 0.05 to about 1, from about 0.05 to about 0.2 mg/kg, or from about 0.05 to about 0.2 mg/kg. In some embodiments where the enantiomer is administered in the recipient animal's feed, the concentration of the enantiomer in the feed (on a 90% dry matter basis) is at least about 0.01 ppm (by weight). For bovine animals, the enantiomer concentration is preferably no greater than about 75 ppm (by weight). In some embodiments, for example, the enantiomer concentration is no greater than about 38 ppm, from about 0.5 to about 20 ppm, from about 3 to about 8 ppm, or from about 3.7 to about 7.5 ppm (by weight). For swine animals, the enantiomer concentration is preferably no greater than about 45 ppm (by weight). In some such embodiments, for example, the concentration is no greater than about 23 ppm, from about 0.5 to about 20 ppm, from about 2 to about 5 ppm, or from about 2.2 to about 4.5 ppm (by weight).

Although single oral daily doses are typically preferred, it is contemplated that shorter or longer periods between doses can be used, depending on, for example, the recipient's metabolism of the enantiomer. It is contemplated that smaller doses may be administered two or more times per day to achieve the desired total daily dose. Such multiple doses per day may, in some instances, be used to increase the total oral daily dose, if desired.

When administered via a subcutaneous implant, the preferred total daily dose of the enantiomer is typically greater than about 0.05 mg/kg (i.e., milligram of enantiomer per kilogram body weight), particularly for bovine and swine animals. In some such embodiments, the daily dose is from about 0.1 to about 0.25 mg/kg.

If the enantiomer composition is administered parenterally via an injection, the concentration of the enantiomer in the dosage form preferably is sufficient to provide the desired therapeutically effective amount of the enantiomer in a volume that is acceptable for parenteral administration. As with oral feeding, an injection dosage form may be administered once per day, although it is contemplated that shorter or longer periods between doses also could be used.

Factors affecting the preferred dosage regimen may include, for example, the type (e.g., species and breed), age, size, sex, diet, activity, and condition of the intended recipient; the type of administration used (e.g., oral via feed, oral via drinking water, subcutaneous implant, other parenteral route, etc.); pharmacological considerations, such as the activity, efficacy, pharmacokinetic, and toxicology profiles of the particular composition administered; and whether the enantiomer is being administered as part of a combination of active ingredients. Thus, the preferred amount of the enantiomer can vary, and, therefore, can deviate from the typical dosages set forth above. Determining such dosage adjustments is generally within the skill of those in the art using conventional means.

It is contemplated that the composition may be administered to the intended recipient a single time. In general, however, the composition is administered over time. In some embodiments where the animal recipient is a livestock animal, for example, the enantiomer is administered daily for at least about 2 days, more typically daily for from about 10 to about 60 days, and still more typically daily for from about 20 to about 40 days. In some particular embodiments, the composition is administered daily for at least about the last 2 days of the finishing period. In some such embodiments, it is administered daily for from about the last 10 to about the last 60 days of the finishing period, or from about the last 20 to about the last 40 days of the finishing period. The term "finishing period" refers to the later stage of the growing period for an animal. During this period, livestock animals are typically confined in a feedlot. In some embodiments where the livestock animal is a bovine animal, this period lasts for from about 90 to about 225 days, and depends on, for example, the starting body weight of the animal. There is typically a withdrawal period following the finishing period in which no zilpaterol enantiomer is administered. The length of this withdrawal period may depend on, for example, the type (e.g., species and breed), age, weight, activity, and condition of the recipient animal, as well as the maximum acceptable enantiomer residue concentration in the meat of the animal.

In some embodiments, the 6R,7R zilpaterol enantiomer is administered in combination with other active ingredients. The administration of the other active(s) typically can be before, simultaneous with, and/or after the administration of the enantiomer. While the enantiomer is typically administered over time, the other active(s) may be administered once, or, alternatively, over an amount of time, which may be the same as or different from the amount of time over which the enantiomer is administered. To the extent that the administration is simultaneous, the combined actives may be part of the same dosage form (e.g., in the same tablet, granule, or powder) and/or separate dosage forms.

In some embodiments (particularly for livestock, such as bovine or swine), the enantiomer is administered with a steroid, such as, for example, a steroid corresponding in structure to Formula (II):

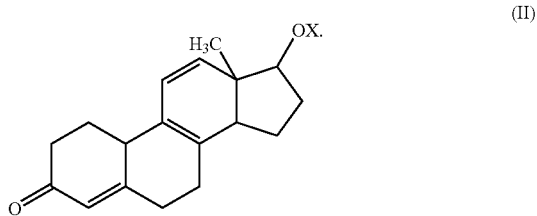

Here, X is hydrogen, $C_1$-$C_6$-alkyl wherein one of the —$CH_2$— groups optionally is replaced with —O—, or an acyl of an organic carboxylic acid having from 1 to about 18 carbon atoms. In some such embodiments, for example, X is —$C(O)CH_3$ (i.e., the steroid comprises trenbolone acetate, also known as "17β-acetoxy-$\Delta^{4,9,11}$-estratriene-3-one"):

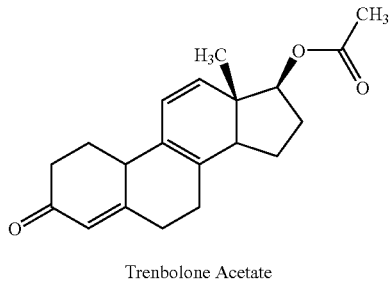

Trenbolone Acetate

The enantiomer also may be administered with, for example, zeranol or estradiol, particularly for livestock. The zeronal or estradiol may be administered orally in the feed. Typically, however, the zeranol or estradiol is administered parenterally, such as via injection or a subcutaneous implant. Suitable locations for a subcutaneous implant include, for example, behind the ear or baleen. The implant is typically implanted for from about 20 days to about 4 months before slaughter, and, more typically, from about 1 to about 3 months before slaughter. The typical total dosage for zeranol is from about 10 to about 100 mg, or from about 10 to about 50 mg. The typical dosage for estradiol is from about 0.05 to about 50 mg. In some embodiments, a steroid (e.g., trenbolone acetate) is administered in addition to the zeranol or estradiol and the 6R,7R enantiomer.

Livestock, poultry, and fish are often confined and fed high-energy finishing diets, particularly as harvest approaches. This can result in a variety of detrimental conditions. Bovine animals, for example, are confined in feedlots and fed high-energy grain diets. This tends to cause lactic ruminal acidosis, which attacks the integrity of the rumen wall. This, in turn, permits opportunistic bacteria (e.g., *Fusobacterium necrophorum* and *Actinomyces pyogenes*) to colonize, enter the bloodstream, and eventually infect the liver and cause liver abscesses. The acidosis itself can be associated with detrimental variances in the daily feed intake, while liver abscesses (particularly severe abscesses) can be associated detrimental decreases in feed intake, daily weight gain, and feed efficiency. See, e.g., U.S. Pat. No. 7,207,289 and citations therein.

In some embodiments, ruminal acidosis and the resulting liver abscesses are reduced or entirely prevented by administering the enantiomer as part of a dosing scheme that also includes administering a therapeutically effective amount of one or more ionophores. Contemplated ionophores include, for example, monensin, lasalocid, laidlomycin propionate, bambermycinand, and salts thereof. Sodium monensin, for example, is marketed under the trade name RUMENSIN®. Determination of an ionophore dosage regimen that is therapeutically effective for the particular type of animal recipient is generally within the skill of the art. When administered properly, ionophores can be effective for increasing feed efficiency and/or improving the rate of body weight gain. It is believed that these effects stem from the effect ionophores have on ruminal fermentation. More specifically, it is believed that ionophores tend to create an environment that inhibits gram-positive lactic-acid-producing bacteria (i.e., *Streptococcus bovis* and *Lactobacillius* spp.), while having no effect on gram-negative lactic-acid-fermenting bacteria. This, in turn, is believed to reduce ruminal acidosis, thereby maintaining the integrity of the rumen wall.

In some embodiments, liver abscesses are reduced or entirely prevented by administering the enantiomer as part of a dosing scheme that also includes administering a therapeutically effective amount of one or more antibiotics. Contemplated antibiotics include, for example, macrolide antibiotics, such as tylosin and salts thereof (tylosin phosphate, for example, is marketed under the trade name TYLAN®). Determination of an antibiotic dosage regimen that is therapeutically effective for the particular type of animal recipient is generally within the skill of the art. When administered properly, antibiotics can be effective for increasing the rate of weight gain, improving feed efficiency, and/or reducing the time for carcass trimming. It is believed that these effects stem from a reduction of opportunistic bacteria (e.g., *Fusobacterium necrophorum* and *Actinomyces pyogenes*) that can infect the liver.

In some embodiments, the enantiomer is administered as part of a dosing scheme that also includes administering one or more ionophores in combination with one or more antibiotics. In these embodiments, the amounts of the one or more ionophores and one or more antibiotics together constitute an amount that is therapeutically effective.

In some embodiments, the enantiomer is administered as part of a dosing scheme that includes administering (e.g., feeding) one or more ionophores and/or one or more antibiotic(s) for a period before the enantiomer is administered. In some such embodiments, the administration of the ionophore(s) and/or antibiotic(s) is ceased when administration (e.g., feeding) of the enantiomer begins. In particularly contemplated embodiments, the ionophore(s) and/or antibiotic(s) is/are administered during a portion of the finishing period before any zilpaterol enantiomer is administered. This is followed by a second period in which the enantiomer is administered without the (or with essentially no) ionophore or antibiotic during the remaining portion of the finishing period. In some such embodiments, administration of the enantiomer begins at least 2 days (or from about 10 to about 60 days, or from about 20 to about 40 days) before the end of the finishing period. To illustrate, it is contemplated that RUMENSIN® and TYLAN® could be fed to a bovine animal throughout the finishing period until the last 40 days of the finishing period, followed by feeding of the enantiomer without RUMENSIN® and TYLAN® for the remaining 40 days of the finishing period. When the enantiomer is administered with "essentially no" ionophore or antibiotic, it is administered without a therapeutically effective amount of any ionophore, antibiotic, or combination thereof.

In some embodiments, the 6R,7R enantiomer is administered with no (or essentially no) other β-2 agonist. When the enantiomer is administered with "essentially no" other β-2 agonist, it is administered without a therapeutically effective amount of any other β-2 agonist.

Unless otherwise indicated, the term "therapeutically effective amount" means an amount sufficient to produce at least a portion of a desired effect discussed in this patent.

EXAMPLES

The following examples are merely illustrative, and not limiting to the remainder of this disclosure in any way.

Example 1

Illustration of a Technique for Isolating the Positive and Negative Trans Zilpaterol Enantiomers Part A. Preparation of racemic trans zilpaterol monohydrochloride. Racemic trans zilpaterol monohydrochloride can be prepared using the method illustrated in Example 13 in Column 11 of Fréchet et al.'s U.S. Pat. No. 4,585,770 (filed Oct. 12, 1983; issued Apr. 29, 1986; incorporated into this patent by reference). The trans enantiomers in the mixture correspond to the following structures:

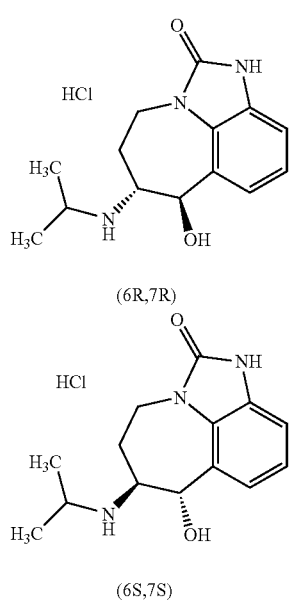

Part B. Preparation of racemic trans zilpaterol free base. An aqueous solution of racemic trans zilpaterol monohydrochloride was treated with AMBERLITE® IRA-67 resin (Fluka Chemie GmbH, Buchs, Switzerland) for 30 minutes, at which time the pH of the solution was determined to be 8. The resin was removed via filtration, and the solution was freeze-dried. The resulting solid was used in the next step without further treatment.

Part C. Separation of trans zilpaterol enantiomers. Freeze-dried product from Part B (1 mg) was dissolved in 0.1 ml ethanol with the aid of an ultrasonic bath. To the resulting clear solution was added 0.9 ml n-hexane, and the resulting solution was filtered. The filtered solution (0.03 ml) was then injected into an HPLC column (CHIRACEL™ OD-H, Chiral Technologies Europe, Illkirch, France) under the following conditions:

| | |
|---|---|
| Internal column diameter | 4.6 mm |
| Column length | 250 mm |
| Packing | Cellulose tris (3,5-dimethylphenylcarbamate) coated on a 5 μm silica support |
| Mobile phase solvent mixture: | n-hexane/ethanol at 90:10 v/v |
| Mobile phase flow rate: | 1 ml/min |
| Mobile phase temperature: | 35° C. |
| Run time: | 15 min |
| Detection: | UV (220 nm) |

The retention times of the two trans enantiomers were as follows:

| Enantiomer | Retention time | Nature of optical rotation |
|---|---|---|
| 1 | 9.9 min | dextrorotatory |
| 2 | 11.7 min | levorotatory |

Optical rotations of the enantiomers were measured using a Perkin Elmer polarimeter 343 (Perkin Elmer, GmbH, Überlingen, Germany).

Example 2

Illustration of a Second Technique for Isolating the Positive and Negative Trans Zilpaterol Enantiomers Part A. Preparation of racemic trans zilpaterol free base. In a 4 L reaction vessel equipped with mechanical stirring was charged zilpaterol hydrochloride (304.6 g, 1.023 mol) and water (1.5 L). An aqueous solution of $NH_4OH$ (20%, 150 mL) was added in portions while stirring. Stirring was then continued at room temperature for 1 hour. The reaction vessel was then placed under stirring in an ice-bath for another hour. This resulted in the formation of a precipitate, which was subsequently collected, washed with water (1 L), washed with petrol ether (500 mL), co-evaporated with toluene, and dried under reduced pressure to afford 256.6 g (96%) of racemic zilpaterol free base as a white solid.

Part B. Preparation of racemic trans zilpaterol benzyl carbamate. A 6 L reaction vessel equipped with mechanical stirring under $N_2$ was charged with product from Step A (125 g, 0.48 mol) and acetone (3.5 L). Sodium bicarbonate (160 g, 1.91 mol) was then added. The resulting suspension was stirred and cooled to 10° C. while benzyl chloroformate (0.59 mol) diluted in toluene (to a total volume of 200 mL) was rapidly added dropwise. After stirring at room temperature for 15 hours, an additional solution of benzyl chloroformate (55 mL, 50% solution in toluene) was added. The resulting mixture was again stirred at room temperature for 15 hours and then filtered. The mother liquor was reserved. Two additional batches (125 and 83 g scale) were then synthesized using the same procedure. The resulting solids were combined and suspended in water (4 L). This mixture was stirred for 30 minutes, and then filtered. The resulting solid was suspended in water (3 L). The mixture was then stirred for 15 minutes, and filtered. The solid was washed with water (2×1 L), petrol ether (500 mL), and diethyl ether (500 mL). This produced a residue, which was dried under reduced pressure to provide 267 g of racemic trans zilpaterol benzyl carbamate as a white solid. The reserved mother liquor was concentrated under vacuum, and the resulting residue was triturated in an aqueous solution at a pH of ≦4 (HCl) to form a precipitate, which, in turn, was rinsed with water and dried under reduced pressure to afford an additional 42 g of racemic trans zilpaterol benzyl carbamate product.

Part C. Separation of the racemic trans zilpaterol benzyl carbamate enantiomers. Product from Step B (as batches of 20-26 g) was dissolved in 1 L of methanol at 50° C. and filtered. The resulting solution was then injected into an LC200 DAC HPLC column (Novasep) under the following conditions, with the first eluting compound being marked as "Isomer A" and the second eluting compound being marked as "Isomer B":

| | |
|---|---|
| Internal column diameter | 200 mm |
| Column length | ~0.60 m |
| Packing | Amylose tris (3,5-dimethylphenylcarbamate) coated on a 20 μm silica support (7.5 kg) |
| Mobile phase | Ethanol |
| Mobile phase flow rate | 18 L/hr |
| Mobile phase temperature | ambient |
| Run time | 1.7 hr |
| Detection | UV (220 nm) |

HPLC was used to analyze the isomer A and isomer B carbamate products under the following conditions:

| | |
|---|---|
| Column | Daicel AD 250 × 4.6 mm |
| Eluent | 100% ethanol |
| Flow rate | 0.8 mL/min |
| Detection | UV (285 nm) |
| Temperature | 25° C. |
| Injection volume | 3 μL with a concentration of 2 mg/mL |

The enantioselectivities ("ee") for the two carbamate products were determined to be as follows:

| Isomer product | ee (%) |
|---|---|
| Isomer A Carbamate | 100 |
| Isomer B Carbamate | 99.3 |

Part D. Formation of the positive trans zilpaterol free base isomer. The isomer A carbamate product from Step C (47 g, 119 mmol), 1,4-dioxane (750 mL), acetic acid (450 mL), water (300 mL), and Pd on carbon (10%, 9.4 g) were charged to a 2 L bomb reactor fitted with magnetic stirring. Following a purge with $N_2$, the mixture was stirred at room temperature for 5 hours under an atmosphere of 4 bars of $H_2$ (adjusted upon consummation of $H_2$). The resulting mixture was filtered through celite, and the resulting solid was washed with 1,4-dioxane. Volatiles were then removed using reduced pressure. A second batch (46 g scale) was then synthesized using the same procedure. The crude product mixtures were then combined, and taken up in a minimum amount of water. The resulting solution was basified with a 30% aqueous solution of $NH_4OH$ to impart a pH of 9-10. This aqueous solution was then successively extracted with 500 mL portions of ethyl acetate. The organic layers were combined, and then dried over magnesium sulphate. After filtration and concentration under reduced pressure, 53 g of the positive trans zilpaterol free base isomer were obtained as a pale yellow solid.

Part E. Formation of the positive trans zilpaterol hydrochloride isomer. Product from Step D (53 g) and ethanol (600 mL) were charged under an inert atmosphere of $N_2$ to a 2 L three-necked round-bottomed flask equipped with a magnetic stirrer, condenser, and thermometer. The mixture was stirred at 70° C. while 20.8 mL (1.25 eq) of concentrated aqueous HCl (12N) were added dropwise. The resulting mixture was stirred at 70° C. for an additional 15 minutes, and then allowed to attain room temperature. The mixture was then cooled with an ice bath, resulting in the formation of a precipitate. The precipitate was filtered, washed with diethyl ether, and dried under reduced pressure to provide 57 g (81% over two steps) of the positive trans zilpaterol hydrochloride isomer as a white solid ($[\alpha]_D$+33 c 1.01 in water, T=20° C.).

Part F. Formation of the negative trans zilpaterol free base isomer. The isomer B carbamate product from Step C (45 g, 114 mmol), 1,4-dioxane (750 mL), acetic acid (450 mL), water (300 mL), and Pd on carbon (10%, 9.0 g) were charged to a 2 L bomb reactor fitted with magnetic stirring. After an initial purge with $N_2$, the mixture was stirred at room temperature for 6 hours under an atmosphere of 5 bars of $H_2$. The resulting mixture was filtered through celite (washed with 1,4-dioxane), and concentrated under reduced pressure to a volume of 200 mL. A second batch (45 g scale) was synthesized using the same procedure. The crude product mixtures were combined, and then basified with NaOH and extracted with ethyl acetate (3×500 mL). The organic layers, in turn, were combined and dried over magnesium sulphate. After filtration and concentration under reduced pressure, 59 g of the negative trans zilpaterol free base isomer were obtained as a pale yellow solid.

Part G. Formation of the negative trans zilpaterol hydrochloride isomer. Product from Step F (59 g) and ethanol (600 mL) were charged to a 1 L three-necked round-bottomed flask equipped with a magnetic stirrer. The resulting mixture was stirred at 70° C. while 24 mL (1.25 eq) of concentrated aqueous HCl (12N) were added dropwise. The mixture was stirred at 70° C. for an additional 15 minutes, and then allowed to attain room temperature. Subsequently, the mixture was cooled with an ice bath to form a precipitate. The precipitate was filtered, washed with diethyl ether, and dried under reduced pressure to provide 55.4 g (82% over two steps) of the negative trans zilpaterol hydrochloride isomer as a white solid ($[\alpha]_D$-33 c 1.03 in water, T=20° C.).

Part H. Determination of the enantioselectivities of the positive and negative trans zilpaterol hydrochloride enantiomer products from Parts E and G.

HPLC was used to analyze the positive and negative trans zilpaterol hydrochloride enantiomer products from Parts E and G under the following conditions:

| | |
|---|---|
| Column | Daicel AD-H 250 × 4.6 mm |
| Eluent | Ethanol with 0.1% diethylamine |
| Flow rate | 0.7 mL/min |
| Detection | UV (295 nm) |
| Temperature | 25° C. |
| Injection volume | 3 μL with a concentration of 2 mg/mL |

The enantioselectivities of the two products were determined to be as follows:

| Product | ee (%) |
|---|---|
| Positive trans zilpaterol hydrochloride enantiomer product from Part E | 100 |
| Negative trans zilpaterol hydrochloride enantiomer product from Part G | 100 |

Example 3

Determination of the Absolute Configuration of (−)-Zilpaterol by X-Ray Crystallography Using a Single Crystal of a Bromophenacyl Derivative Part A. Synthesis of trans(−) 4,5,6,7-tetrahydro-7-hydroxy-6-[(1-methyl-ethyl)amino]-1-(4-bromophenacyl)-imidazo[4,5,1-jk][1]benzazepin-2(1H)-one (C).

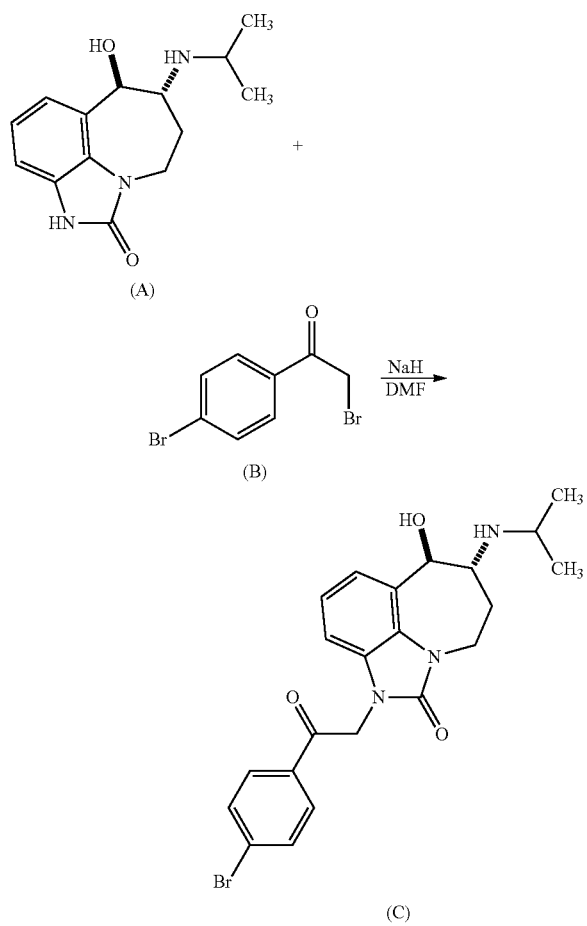

To a solution of 0.75 g of (−)-zilpaterol free base (A) in 15 mL of dry N,N-dimethylformamide (DMF) was added 172 mg of solid sodium hydride (60% dispersion in mineral oil). Ten minutes later, 956 mg of 2,4'-dibromoacetophenone (B) was added. The resulting reaction mixture was stirred for 20 hours at ambient temperature. Water was then added. The resulting solution was extracted twice with diethyl ether, and the combined organic layers were washed three times with sodium bicarbonate solution (5%). After drying over magnesium sulphate, the organic phase was evaporated to dryness, and the residue was purified by column chromatography on silica gel (dichloromethane/methanol 9:1 v/v). The bromophenacyl derivative (C) was obtained as a bright yellow solid (0.66 g, 50%): m.p. 169-170° C. (dec., from ethanol); $[\alpha]_D=-27°$ (c 0.446, ethanol, T=20° C.); $v_{max}/cm^{-1}$ (neat) 3331, 2962, 2925, 1692, 1586, 1425, 1223, 1072, 984, 831, 748, 738, 700; $\delta_H$ (300 MHz, DMSO-d$_6$) 1.00 (d, J=6.2 Hz, 3H), 1.03 (d, J=6.2 Hz, 3H), 1.70-1.83 (m, 1H), 2.20-2.36 (m, 1H), 2.91 (sp, J=6.2 Hz, 1H), 3.08-3.16 (m, 1H), 3.83-3.99 (m, 2H), 4.59 (d, J=6.4 Hz, 1H), 5.48 (b, 2H), 6.98 (dd, J=7.7 Hz, J=7.7 Hz, 1H), 7.03 (dd, J=7.7 Hz, J=1.3 Hz, 1H), 7.11 (dd, J=7.5 Hz, J=1.2 Hz, 1H), 7.83 (d, J=8.6 Hz, 2H), 8.04 (d, J=8.6 Hz, 2H); $\delta_C$ (75 MHz, DMSO-d$_6$) 22.5, 23.8, 28.4, 39.6, 44.9, 47.4, 58.3, 73.8, 107.1, 120.4, 122.5, 124.4, 126.4, 128.2, 129.6, 130.2 (2), 131.9 (2), 133.4, 153.8, 192.7; m/z (APCI) 460.1 (M+H$^+$).

Part B. X-ray analysis of trans(−) 4,5,6,7-tetrahydro-7-hydroxy-6-[(1-methyl-ethyl)amino]-1-(4-bromophenacyl)-imidazo[4,5,1-jk][1]benzazepin-2(1H)-one (C). A single crystal of the trans(−)-zilpaterol derivative (C) was obtained from an ethanolic solution, and x-ray analysis revealed the absolute configuration of the amino alcohol moiety to be 6R,7R. Thus, it follows that the trans(−) zilpaterol isomer (A) also has the 6R,7R configuration.

Example 4

Evaluation of Adrenergic β$_2$ Receptor Agonist Activity of the Trans Zilpaterol Monohydrochloride Racemic Mixture and Individual Enantiomers Using an In Vitro Binding Assay In this experiment, an in vitro radioligand binding assay was used to determine the affinities of racemic trans zilpaterol and its individual enantiomers with respect to the recombinant human β$_2$ adrenergic receptor in transfected Sf-9 cells.

A. Experimental Procedure

In vitro pharmacology binding assays for human β$_2$ adrenergic receptor in transfected Sf9 cells are generally described in, for example, Smith et al., "Beta-blocker selectivity at cloned human beta1- and beta2-adrenergic receptors," *Cardiovasc. Drugs Ther.*, 13, 123 (1999).

Cell membrane homogenates (15-20 μg protein) were incubated for 60 min at 22° C. with 0.15 nM [3H]CGP 12177 (this compound is a standard for this β$_2$ binding assay, and is commercially available from various sources, including PerkinElmer and Amersham Int'l) in the absence or presence of the test compound in a buffer containing 50 mM Tris-HCl (pH 7.4), 10 mM MgCl$_2$, and 2 mM EDTA. The standard reference antagonist was ICI 118551 (commercially available from various sources, including Sigma-Aldrich, Tocris Bioscience, and BIOMOL Int'l LP), which was tested in each experiment at several concentrations to obtain a competition curve from which its IC$_{50}$ was calculated.

Non-specific binding was determined in the presence of 50 μM alprenolol. Following incubation, the samples were filtered rapidly under vacuum through glass fiber filters (GF/B, Packard) pre-soaked with 0.3% PEI, and rinsed several times with ice-cold 50 mM Tris-HCl using a 96-sample cell harvester (Unifilter, Packard). The filters were dried, and counted for radioactivity in a scintillation counter (Topcount, Packard) using a scintillation cocktail (Microscint 0, Packard). The results are expressed as percent inhibition of the control radioligand specific binding.

Specific ligand binding to the receptors is the difference between the total binding and the non-specific binding determined in the presence of an excess of unlabelled ligand. The results are expressed as a percent of control specific binding and as a percent inhibition of control specific binding obtained in the presence of the test compounds.

The $IC_{50}$ values (concentration causing a half-maximal inhibition of control specific binding) and Hill coefficients (nH) were determined by non-linear regression analysis of the competition curves using Hill equation curve fitting. The inhibition constants ($K_i$) were calculated from the Cheng Prusoff equation:

$$K_i = IC50/(1+(L/KD))$$

Here, L is the concentration of radioligand in the assay, and KD is the affinity of the radioligand for the receptor.

B. Results

Tables 1 and 2 summarize the binding effects of the 6S,7S zilpaterol enantiomer, 6R,7R zilpaterol enantiomer, and racemic trans zilpaterol observed with respect to the human $\beta_2$ adrenergic receptor. The binding assay was repeated to confirm reliability of the data. Table 1 summarizes the results from the first assay, and Table 2 summarizes the results from the repeat assay. Each run within each assay was conducted in duplicate. Tables 1 and 2 provide the binding data from each of the runs, as well as the mean values of that data.

TABLE 1

Results of First In Vitro Binding Assay

| Compound | Test concentration (M) | % Inhibition of control specific binding | % of control specific binding | | |
|---|---|---|---|---|---|
| | | | Run 1 | Run 2 | Mean |
| 6S,7S enantiomer | 1.0E−05 | 3 | 98.9 | 95.7 | 97.3 |
| 6R,7R enantiomer | 1.0E−05 | 94 | 9.3 | 2.6 | 5.9 |
| Racemic trans | 1.0E−05 | 90 | 11.9 | 8.7 | 10.3 |

TABLE 2

Results of Repeat In Vitro Binding Assay

| Compound | Test concentration (M) | % Inhibition of control specific binding | % of control specific binding | | |
|---|---|---|---|---|---|
| | | | Run 1 | Run 2 | Mean |
| 6S,7S enantiomer | 1.0E−05 | 6 | 97.2 | 91.3 | 94.2 |
| 6R,7R enantiomer | 1.0E−05 | 83 | 18.3 | 15.3 | 16.8 |
| Racemic trans | 1.0E−05 | 80 | 21.3 | 18.6 | 20.0 |

The $IC_{50}$ and $K_i$ value for the reference antagonist, ICI 118551, from three independent experiments are provided in Table 3. This data is within ±0.5 log units. Applicants believe this corroborates the reliability of the assay results.

TABLE 3

$IC_{50}$ and $K_i$ Values Observed for the Reference Antagonist, ICI 118551

| $IC_{50}$ (M) | $K_i$ (M) | $n_H$ |
|---|---|---|
| 2.3E−09 | 1.1E−09 | 1.7 |
| 3.4E−09 | 1.8E−09 | 1.4 |
| 3.3E−09 | 1.7E−09 | 1.7 |

Table 4 provides the observed binding data of the 6R,7R zilpaterol enantiomer and racemic trans zilpaterol. As can be seen, each run was conducted in duplicate. Table 4 provides the individual data of each run, as well as the mean values of the data.

TABLE 4

Individual Binding Data of the 6R,7R Zilpaterol Enantiomer and Racemic Trans Zilpaterol Used to Determine $IC_{50}$ and $K_i$ Values in Table 5

| Test Compound | Concentration (M) | % of Control Specific Binding | | |
|---|---|---|---|---|
| | | Run 1 | Run 2 | Mean |
| 6R,7R Enantiomer | 1.0E−09 | 122.2 | 140.2 | 131.2 |
| 6R,7R Enantiomer | 1.0E−08 | 132.6 | 126.9 | 129.7 |
| 6R,7R Enantiomer | 3.0E−08 | 91.1 | 114.6 | 102.8 |
| 6R,7R Enantiomer | 1.0E−07 | 105.3 | 106.0 | 105.7 |
| 6R,7R Enantiomer | 3.0E−07 | 89.5 | 90.4 | 89.9 |
| 6R,7R Enantiomer | 1.0E−06 | 46.6 | 51.8 | 49.2 |
| 6R,7R Enantiomer | 3.0E−06 | 17.6 | 24.0 | 20.8 |
| 6R,7R Enantiomer | 3.0E−05 | 9.8 | 5.8 | 7.8 |
| Racemic trans | 1.0E−09 | 137.5 | 136.1 | 136.8 |
| Racemic trans | 1.0E−08 | 132.4 | 132.4 | 132.4 |
| Racemic trans | 3.0E−08 | 141.7 | 141.7 | 141.7 |
| Racemic trans | 1.0E−07 | 116.8 | 131.4 | 124.1 |
| Racemic trans | 3.0E−07 | 104.4 | 102.0 | 103.2 |
| Racemic trans | 1.0E−06 | 70.0 | 74.5 | 72.3 |
| Racemic trans | 3.0E−06 | 38.5 | 48.6 | 43.6 |
| Racemic trans | 3.0E−05 | 10.5 | 6.3 | 8.4 |

Table 5 shows the $IC_{50}$ and $K_i$ value for the 6R,7R zilpaterol enantiomer and racemic trans zilpaterol calculated from the data in Table 4. The $IC_{50}$ determination for the 6S,7S zilpaterol enantiomer was not performed due to its weak binding at 10 μM.

TABLE 5

$IC_{50}$ and $K_i$ Values Observed for the 6R,7R Zilpaterol Enantiomer and Racemic Trans Zilpaterol

| Compound | $IC_{50}$ (M) | $K_i$ (M) | $n_H$ |
|---|---|---|---|
| 6R,7R Enantiomer | 6.2E−07 | 3.2E−07 | 0.9 |
| Racemic trans | 1.1E−06 | 5.8E−07 | 0.9 |

C. Conclusion

Applicants have conducted binding assays to determine the adrenergic β2 receptor agonist activities of racemic trans zilpaterol monohydrochloride, as well as the separate trans zilpaterol isomers. The results indicate that the adrenergic $\beta_2$ agonist activity of racemic trans zilpaterol monohydrochloride essentially stems from the 6R,7R enantiomer alone, and that the 6S,7S, enantiomer has relatively negligible adrenergic β2 receptor activity ($IC_{50}$>10 μM). As shown in Table 4, the observed $IC_{50}$'s for the racemic mixture and the 6R,7R enantiomer alone with respect to recombinant human $\beta_2$ adrenergic receptor were 1.1 μM and 0.62 μM, respectively. Applicants believe that the ~2-fold difference between these values stems from the fact that the 6R,7R enantiomer concentration in racemic trans zilpaterol is about 50%.

Example 5

Evaluation of Adrenergic $\beta_2$ Receptor Agonist Activity of the Trans Zilpaterol Monohydrochloride Racemic Mixture and Individual Enantiomers Using In this experiment, $\beta_2$ adrenergic receptor agonist activities were functionally determined using a quantitative ex-vivo guinea pig trachea bioassay.

A. Experimental Procedure

Functional ex-vivo pharmacology assays for the $\beta_2$ adrenergic receptor are generally described in, for example, O'Donell, et al., "The importance of choice of agonists in studies designed to predict $\beta1:\beta2$ adrenoceptor selectivity of antagonists from pA2 values on guinea-pig trachea and atria," *Naunyn-Scmiedeberg's Arch. Pharmacol.*, 308, 183 (1979).

Rings of guinea pig trachea were suspended in 20-ml organ baths containing an oxygenated (95% $O_2$ and 5% $CO_2$) and pre-warmed (37° C.) physiological salt solution having a pH of 7.4 and the following composition: NaCl 118.0 mM, KCl 4.7 mM, $MgSO_4$ 1.2 mM, $CaCl_2$ 2.5 mM, $KH_2PO_4$ 1.2 mM, $NaHCO_3$ 25 mM, and glucose 11.0 mM. In addition, CGS 15943 (1 µM; this is commercially available from various sources, including Research Biochemicals Int'l and Sigma-Aldrich), benextramine (1 µM), pyrilamine (1 µM), cimetidine (10 µM), methysergide (1 µM), and indomethacin (3 µM) were present to block the adenosine A2, α-adrenergic, histamine H1, histamine H2 and 5-HT2 receptors, and to prevent prostanoid release. The tissues were exposed to a single effective concentration of the respective reference agonist to verify responsiveness and to obtain a control response. Following extensive washings and recovery to the initial state, the tissues were exposed to a single or several cumulative concentrations of the test compounds or the same agonist. Each concentration was left in contact with the tissues until a stable response was obtained. When an agonist-like response was obtained, the respective reference antagonist was tested against the test compounds to confirm the involvement of the receptor studied in this response. The experiments were carried out using semi-automated isolated organ systems possessing eight organ baths, with multi-channel data acquisition. Assay volume and format was 20 ml organ baths. Each test compound was added as a 100-fold concentrated solution in $H_2O$ or 1000-fold concentrated solution in DMSO. The maximum tolerable DMSO concentration was 0.1%.

To test for agonist activity, the tissues were contracted with carbachol (0.1 µM), and then exposed to a sub-maximal concentration of the reference agonist salbutamol (0.3 µM) to verify responsiveness and to obtain a control relaxation. Following washings, the tissues were contracted again with carbachol, and then exposed to increasing concentrations of the test compound or the same agonist. The different concentrations were added cumulatively, and each left in contact with the tissues until a stable response was obtained or for a maximum of 20 min. If an agonist-like response (relaxation) was obtained, the reference antagonist, ICI 118551 (0.3 µM), was tested against the highest concentration of the compound to confirm the involvement of the $\beta_2$ receptors in the response.

To test for antagonist activity, the tissues are contracted with carbachol (0.1 µM), and then exposed to a sub-maximal concentration of the reference agonist salbutamol (0.3 µM) to obtain a control relaxation. After stabilization of the salbutamol-induced relaxation, increasing concentrations of the test compound or the reference antagonist, ICI 118551, were added cumulatively. Each concentration was left in contact with the tissues until a stable response was obtained or for a maximum of 20 min. If it occurred, a recovery of contraction by the test compound indicated an antagonist activity at the $\beta_2$ receptors.

The parameter measured was the maximal change in tension induced by each compound concentration. The results were in the form of percent variation of the control response to the reference agonist (mean values). The agonist efficacy and potency of the test compounds were evaluated respectively in terms of $E_{max}$ values (maximum response) and $EC_{50}$ values (concentration producing a half-maximum response). These were determined from the concentration-response curves.

B. Results

Table 6 shows the observed effects of the 6S,7S zilpaterol enantiomer, 6R,7R zilpaterol enantiomer, and racemic trans zilpaterol with respect to agonist activity at the adrenergic $\beta_2$ receptor in isolated organ bioassays at a concentration of 10 µM. Table 6 also shows the observed effects of the reference agonist, salbutamol, at concentrations of 0.003, 0.03, and 0.3 µM.

TABLE 6

Agonist Activity at the $\beta_2$ Adrenergic Receptors in Guinea Pig Trachea

| Compounds | Concentration (M) | Percent of the Control Response to Salbutamol at 3.0E−07 M | | |
|---|---|---|---|---|
| | | Run 1 | Run 2 | Mean |
| 6S,7S enantiomer | 1.0E−05 | 28 | 28 | 28 |
| +ICI 118551 | 3.0E−07 | 36 | 32 | 34 |
| 6R,7R enantiomer | 1.0E−05 | 113 | 90 | 102 |
| +ICI 118551 | 3.0E−07 | 25 | 32 | 29 |
| Racemic Trans | 1.0E−05 | 111 | 100 | 106 |
| +ICI 118551 | 3.0E−07 | 26 | 11 | 19 |
| Salbutamol | 3.0E−09 | | | 8 |
| Salbutamol | 3.0E−08 | | | 50 |
| Salbutamol | 3.0E−07 | | | 101 |
| +ICI 118551 | 3.0E−07 | | | 2 |

Table 7 shows the observed effects of the 6S,7S zilpaterol enantiomer, 6R,7R zilpaterol enantiomer, and racemic trans zilpaterol with respect to agonist activity at the adrenergic $\beta_2$ receptor in isolated organ bioassays at various concentrations. Table 7 also shows the observed effects of the reference agonist, salbutamol, at concentrations of 0.003, 0.03, and 0.3 µM.

TABLE 7

Agonist Activities with Increasing Concentrations at the $\beta_2$ Adrenergic Receptors in Guinea Pig Trachea

| Compounds | Concentration (M) | Percent of the Control Response to Salbutamol at 3.0E−07 M | | |
|---|---|---|---|---|
| | | Run 1 | Run 2 | Mean |
| 6S,7S Enantiomer | 1.0E−07 | 0 | 0 | 0 |
| | 3.0E−07 | 4 | 5 | 5 |
| | 1.0E−06 | 10 | 11 | 11 |
| | 3.0E−06 | 26 | 23 | 25 |
| | 1.0E−05 | 58 | 54 | 56 |
| | 3.0E−05 | 92 | 94 | 93 |
| | 1.0E−04 | 103 | 105 | 104 |
| | 3.0E−04 | 104 | 105 | 105 |

TABLE 7-continued

Agonist Activities with Increasing Concentrations at the $\beta_2$ Adrenergic Receptors in Guinea Pig Trachea

| Compounds | Concentration (M) | Percent of the Control Response to Salbutamol at 3.0E−07 M | | |
|---|---|---|---|---|
| | | Run 1 | Run 2 | Mean |
| +ICI 118551 | 1.0E−06 | 17 | 18 | 18 |
| 6R,7R Enantiomer | 1.0E−10 | 0 | 0 | 0 |
| | 3.0E−10 | 0 | 0 | 0 |
| | 1.0E−09 | 6 | 5 | 6 |
| | 3.0E−09 | 16 | 18 | 17 |
| | 1.0E−08 | 46 | 47 | 47 |
| | 3.0E−08 | 89 | 88 | 89 |
| | 1.0E−07 | 103 | 100 | 102 |
| | 3.0E−07 | 103 | 100 | 102 |
| +ICI 118551 | 1.0E−06 | 5 | 7 | 6 |
| Racemic Trans | 1.0E−10 | 0 | 0 | 0 |
| | 3.0E−10 | 1 | 1 | 1 |
| | 1.0E−09 | 5 | 7 | 6 |
| | 3.0E−09 | 12 | 16 | 14 |
| | 1.0E−08 | 30 | 37 | 34 |
| | 3.0E−08 | 69 | 76 | 73 |
| | 1.0E−07 | 95 | 100 | 98 |
| | 3.0E−07 | 100 | 100 | 100 |
| +ICI 118551 | 1.0E−06 | 15 | 16 | 16 |
| Salbutamol | 3.0E−09 | | | 11 |
| | 3.0E−08 | | | 53 |
| | 3.0E−07 | | | 104 |
| +ICI 118551 | 3.0E−07 | | | 5 |

Table 8 shows the $E_{max}$ and $EC_{50}$ values determined for the 6S,7S zilpaterol enantiomer, 6R,7R, zilpaterol enantiomer, and racemic trans zilpaterol.

TABLE 8

$E_{max}$ and $EC_{50}$ values at the $\beta_2$ adrenergic receptors in isolated organ bioassays

| Compounds | $E_{max}$ (%) | $EC_{50}$ (M) |
|---|---|---|
| 6S,7S Enantiomer | 105 | 6.9E−06 |
| 6R,7R Enantiomer | 102 | 8.7E−09 |
| Racemic trans | 100 | 1.3E−08 |

C. Conclusion

The potency of the 6R,7R enantiomer with respect to $\beta_2$ agonistic activity was about three orders of magnitude greater than that of the 6S,7S enantiomer. Specifically, in the functional pharmacology assays (ex-vivo Guinea pig trachea), the $EC_{50}$ of the 6R,7R enantiomer was 8.7 nM. The $EC_{50}$ of racemic trans zilpaterol was 13 nM. And the $EC_{50}$ of the 6S,7S enantiomer was 6.9 μM.

Example 6

Evaluation of μ-Opioid Receptor Binding of 6S,7S Zilpaterol Enantiomer, 6R,7R Zilpaterol Enantiomer, and Racemic Trans Zilpaterol The purpose of this study was to investigate the affinity of the 6S,7S zilpaterol-HCl enantiomer, 6R,7R zilpaterol-HCl enantiomer, and racemic trans zilpaterol-HCl toward the human α-receptor (MOP) agonist site in transfected HEK-293 cells. This investigation was conducted using a radioligand binding assay.

A. Experimental Procedure

In-vitro pharmacology binding assays for the β-receptor agonist site are generally described in, for example, Wang, et al., "Human μ-opiate receptor; cDNA and genomic clones, pharmacological characterization and chromosomal assignment," *FEBS Lett.*, 338, 217-222 (1994).

Cell membrane homogenates (75 μg protein) were incubated for 120 min at 22° C. with 0.5 nM [3H]DAMGO (this compound is a standard for this μ-opioid receptor binding assay, and is commercially available from Amersham Int'l) in the absence or presence of the test compound in a buffer containing 50 mM Tris-HCl (pH 7.4) and 5 mM $MgCl_2$. The standard reference compound was DAMGO, which was tested in each experiment at several concentrations to obtain a competition curve from which its $IC_{50}$ is calculated.

Non-specific binding was determined in the presence of 10 μM naloxone. Assay volume and format was 250 μl in 96-well plate. The test compound was added as a 10-fold concentrated solution, and the maximum tolerable DMSO concentration was 1%. Following incubation, the samples were filtered rapidly under vacuum through glass fiber filters (GF/B, Packard), pre-soaked with 0.3% PEI, and rinsed several times with ice-cold 50 mM Tris-HCl using a 96-sample cell harvester (Unifilter, Packard). The filters were dried, and counted for radioactivity in a scintillation counter (Topcount, Packard) using a scintillation cocktail (Microscint 0, Packard). The results were expressed as percent inhibition of the control radioligand specific binding.

Specific ligand binding to the receptors is the difference between the total binding and the non-specific binding determined in the presence of an excess of unlabelled ligand. The results are expressed as a percent of control specific binding and as a percent inhibition of control specific binding obtained in the presence of the test compounds.

The $IC_{50}$ values (concentration causing a half-maximal inhibition of control specific binding) and Hill coefficients (nH) were determined by non-linear regression analysis of the competition curves using Hill equation curve fitting. The inhibition constants ($K_i$) were calculated from the Cheng Prusoff equation:

$$K_i = IC50/(1+(L/KD)).$$

Here, L is the concentration of radioligand in the assay, and KD is the affinity of the radioligand for the receptor.

B. Results

Tables 9 and 10 summarize the binding effects of the 6S,7S zilpaterol enantiomer, 6R,7R zilpaterol enantiomer, and racemic trans zilpaterol observed with respect to the human μ-opioid receptor. The binding assay was repeated to confirm reliability of the data. Table 9 summarizes the results from the first assay, and Table 10 summarizes the results from the repeat assay. Each run within each assay was conducted in duplicate. Tables 9 and 10 provide the binding data from each of the runs, as well as the mean values of that data.

TABLE 9

Results of First Human μ-Opioid Receptor Binding Assay

| Compound | Test Concentration (M) | % Inhibition of Control Specific Binding | % of Control Specific Binding | | |
|---|---|---|---|---|---|
| | | | Run 1 | Run 2 | Mean |
| 6S,7S enantiomer | 1.0E−05 | 34 | 67.2 | 65.4 | 66.3 |
| 6R,7R enantiomer | 1.0E−05 | 7 | 90.8 | 95.0 | 92.9 |
| Racemic trans | 1.0E−05 | 24 | 76.2 | 76.2 | 76.2 |

TABLE 10

Results of Repeat Human μ-Opioid Receptor Binding Assay

| Compound | Test Concentration (M) | % Inhibition of Control Specific Binding | % of Control Specific Binding | | |
|---|---|---|---|---|---|
| | | | Run 1 | Run 2 | Mean |
| 6S,7S enantiomer | 1.0E−03 | 100 | 0.1 | 0.4 | 0.2 |
| 6R,7R enantiomer | 1.0E−03 | 82 | 17.8 | 18.0 | 17.9 |
| Racemic trans | 1.0E−03 | 98 | 1.6 | 2.9 | 2.2 |

The $IC_{50}$ and $K_i$ value for the reference compound, DAMGO, from three independent experiments are provided in Table 11. This data is within ±0.5 log units. Applicants believe this corroborates the reliability of the assay results.

TABLE 11

$IC_{50}$ and $K_i$ Values Observed for the Reference Compound, DAMGO

| $IC_{50}$ (M) | $K_i$ (M) | $n_H$ |
|---|---|---|
| 8.4E−10 | 3.4E−10 | 1.0 |
| 6.6E−10 | 2.7E−10 | 0.9 |
| 7.1E−10 | 2.9E−10 | 0.9 |

Table 12 provides the observed binding data of the 6S,7S zilpaterol enantiomer, 6R,7R zilpaterol enantiomer, and racemic trans zilpaterol. As can be seen, each run was conducted in duplicate. Table 12 provides the individual data from each run, as well as the mean values of the data.

TABLE 12

Binding Data of the 6S,7S Zilpaterol Enantiomer, 6R,7R Zilpaterol Enantiomer, and Racemic Trans Zilpaterol Used to Determine the $IC_{50}$ and $K_i$ Values in Table 13

| Compound | Test Concentration (M) | % of Control Specific Binding | | |
|---|---|---|---|---|
| | | Run 1 | Run 2 | Mean |
| 6S,7S Enantiomer | 3.0E−08 | 93.9 | 97.7 | 95.8 |
| 6S,7S Enantiomer | 3.0E−07 | 97.5 | 93.2 | 95.3 |
| 6S,7S Enantiomer | 1.0E−06 | 90.9 | 84.6 | 87.7 |
| 6S,7S Enantiomer | 3.0E−06 | 81.0 | 77.2 | 79.1 |
| 6S,7S Enantiomer | 1.0E−05 | 61.1 | 59.2 | 60.2 |
| 6S,7S Enantiomer | 3.0E−05 | 34.9 | 37.2 | 36.1 |
| 6S,7S Enantiomer | 1.0E−04 | 15.9 | 16.9 | 16.4 |
| 6S,7S Enantiomer | 1.0E−03 | 1.4 | 0.9 | 1.2 |
| 6R,7R Enantiomer | 3.0E−07 | 94.8 | 92.4 | 93.6 |
| 6R,7R Enantiomer | 1.0E−06 | 91.1 | 87.5 | 89.3 |
| 6R,7R Enantiomer | 3.0E−06 | 92.1 | 88.7 | 90.4 |
| 6R,7R Enantiomer | 1.0E−05 | 80.4 | 82.1 | 81.3 |
| 6R,7R Enantiomer | 3.0E−05 | 73.9 | 87.5 | 80.7 |
| 6R,7R Enantiomer | 1.0E−04 | 71.3 | 70.8 | 71.1 |
| 6R,7R Enantiomer | 3.0E−04 | 46.6 | 40.4 | 43.5 |
| 6R,7R Enantiomer | 1.0E−03 | 23.0 | 25.2 | 24.1 |
| Racemic trans | 3.0E−08 | 105.8 | 90.9 | 98.3 |
| Racemic trans | 3.0E−07 | 92.1 | 90.4 | 91.2 |
| Racemic trans | 1.0E−06 | 84.9 | 95.1 | 90.0 |
| Racemic trans | 3.0E−06 | 76.2 | 87.4 | 81.8 |
| Racemic trans | 1.0E−05 | 76.7 | 70.8 | 73.7 |
| Racemic trans | 3.0E−05 | 49.3 | 45.6 | 47.5 |
| Racemic trans | 1.0E−04 | 24.5 | 22.9 | 23.7 |
| Racemic trans | 1.0E−03 | 2.4 | 3.3 | 2.9 |

Table 13 shows the $IC_{50}$ and $K_i$ value for the 6S,7S zilpaterol enantiomer, 6R,7R zilpaterol enantiomer, and racemic trans zilpaterol calculated from the data in Table 12.

TABLE 13

$IC_{50}$ and $K_i$ Values Observed for the 6S,7S Zilpaterol Enantiomer, 6R,7R Zilpaterol Enantiomer, and Racemic Trans Zilpaterol

| Compound | $IC_{50}$ (M) | $K_i$ (M) | $n_H$ |
|---|---|---|---|
| 6S,7S Enantiomer | 1.7E−05 | 7.0E−06 | 0.9 |
| 6R,7R Enantiomer | 3.2E−04 | 1.3E−04 | 0.9 |
| Racemic trans | 3.1E−05 | 1.3E−05 | 0.9 |

C. Conclusion

The 6R,7R zilpaterol enantiomer binds weakly to the μ-opioid receptor, whereas 6S,7S enantiomer and racemic trans Zilpaterol exhibited greater binding. More specifically, there is a 10-fold difference between the $K_i$ values of the 6R,7R zilpaterol enantiomer vs. racemic trans zilpaterol (i.e., 130 μM vs. 13 μM), and greater than an 18-fold difference in the $K_i$ values between the 6R,7R zilpaterol enantiomer and 6S,7S zilpaterol enantiomer (i.e., 130 μM vs. 7 μM). In addition, there is more than a 10-fold difference between the $IC_{50}$'s of the 6R,7R zilpaterol enantiomer and racemic trans zilpaterol (i.e., 320 μM vs. 31 μM), and more than an 18-fold difference between the $IC_{50}$'s of the 6R,7R zilpaterol enantiomer and 6S,7S zilpaterol enantiomer (i.e., 320 μM vs. 17 μM).

As demonstrated in Examples 4 and 5, the 6R,7R zilpaterol enantiomer appears to account for essentially all the $β_2$ agonist activity of racemic trans zilpaterol. And, as shown in this Example 6, the 6R,7R zilpaterol enantiomer provides this activity while also having a reduced affinity to bind to the μ-opioid receptor. It is suggested in the art that less μ-opioid receptor affinity may generally coincide with various advantageous effects. Accordingly, it is contemplated that the 6R,7R enantiomer may provide one or more of such advantageous effects over racemic trans zilpaterol. Contemplated benefits include, for example, greater feed intake, which, in turn, results in greater body weight gain and/or a greater growth rate. Other contemplated benefits include, for example, greater gastrointestinal motility, greater lung ventilation, greater alertness, greater wakefulness, and/or undisturbed thermoregulation.

Functional ex-vivo isolated organ bioassays also have been conducted to evaluate the μ-opioid receptor agonist response from the 6R,7R zilpaterol enantiomer, 6S,7S zilpaterol enantiomer, and racemic trans zilpaterol. Functional ex-vivo pharmacology assays on the μ-opioid receptor are generally described in, for example, Hutchinson, et al. "Assessment in the guinea-pig ileum and mouse vas deferens of benzomorphans which have strong antinociceptive activity but not substitute for morphine in the dependent monkey." *Brit. J. Pharmacol.*, 55, 541-546 (1975). The results of the functional assays did not correlate to the μ-opioid receptor binding data described above. In contrast, the results showed the 6R,7R zilpaterol enantiomer to have a greater μ-opioid agonist response than both the 6S,7S zilpaterol enantiomer and racemic trans zilpaterol. Applicants believe that the results from the functional assays may be faulty due to problems associated with the assays. Specifically, Applicants believe that the μ-opioid response in the functional assays may have been displaced by, for example, the beta-agonistic effects of the compounds in the isolated organs (i.e., Guinea pig ileum). This belief is supported by the fact that the observed agonist response in the functional assays was poorly reversed by the μ-opioid receptor antagonist, naloxone. The poor reversal of the observed agonist response suggests that at least part of the observed agonist response was due to other targets (e.g., $\beta_2$ receptors) in the isolated organs rather than the μ-opioid receptor.

Example 7

Illustration of a Contemplated Suitable Dosage Form

A tablet is prepared containing 2.5 or 5 mg of the 6R,7R zilpaterol enantiomer, and sufficient excipient of lactose, wheat starch, treated starch, rice starch, talc, and magnesium stearate for a final weight of 100 mg.

Example 8

Further Illustration of a Contemplated Suitable Dosage Form

Granules are prepared containing 12.5 or 25 of the 6R,7R zilpaterol enantiomer in each daily dose of granules.

Example 9

Further Illustration of a Contemplated Suitable Dosage Form

The 6R,7R zilpaterol enantiomer is crystallized using the methodology discussed U.S. Pat. No. 5,731,028 for making crystalline racemic trans zilpaterol. Less than 5% of the crystals have a size of less than 15 μm, and at least 95% of the crystals have a size of less than 250 μm. A premix of the crystalline 6R,7R enantiomer secured to a 300-800 μm corn cob support is then obtained using the methodology discussed in European Patent 0197188 (inventor: Grabitz; filed Oct. 7, 1985; grant published May 31, 1989; incorporated by reference into this patent). The concentration of the 6R,7R enantiomer in the premix is 3% (by weight).

Example 10

Illustration of Evaluating Efficacy of the 6R,7R Zilpaterol Enantiomer

Efficacy of the 6R,7R zilpaterol enantiomer in bovine animals may be evaluated (alone or in combination with other therapeutics) using various protocols. This example illustrates one such protocol. Here, the bovine animals are divided into four groups:

Group 1. 10 bovine animals. Each bovine animal in Group 1 is a control, and receives no zilpaterol compound in the feed.

Group 2. 10 bovine animals. Each bovine animal in Group 2 receives 0.2 mg/kg of the 6R,7R enantiomer per day in the feed.

Group 3. 10 bovine animals. Each bovine animal in Group 3 receives 0.2 mg/kg of 6R,7R enantiomer per day in the feed, and has an implant containing 20 mg trenbolone acetate and 36 mg zeranol.

Group 4. 10 bovine animals. Each bovine animal in Group 4 receives no zilpaterol compound in the feed, but does have an implant containing 20 mg trenbolone acetate and 36 mg zeranol.

Before conducting this study, all the bovine animals are fed the same feed for 90 days. The implants in Groups 3 and 4 are placed into the subcutaneous tissue in the rear of the ear. The study is conducted over 28 days. The weight of each bovine animal at the beginning and end are measured, as well as the amount of feed consumed by each bovine animal during the study. From this, the average daily weight gain, average total weight gain, and feed efficiency for each group is calculated and compared.

This example is merely an illustration showing how the 6R,7R enantiomer may be evaluated. Although this illustration uses bovine animals, a skilled artisan can generally use the protocol with any other species (e.g., swine, lambs, etc.). A skilled artisan also can generally use this protocol to evaluate combination therapies other than with trenbolone acetate and zeranol.

Example 11

Illustration of Evaluating Carcass Leanness

The effect of the 6R,7R zilpaterol enantiomer on carcass leanness may be evaluated using, for example, the following illustrative protocol. Heifers and steers are fed a finishing diet during the pretreatment phase for at least 85 days before being treated with the 6R,7R enantiomer. Feeding of the enantiomer begins either 20 or 40 days before slaughter. The cattle are withdrawn from the 6R,7R enantiomer for 5 days before slaughter. The cattle are fed a variety of diets that range in NEg from 62.3 to 70.9 Mcal/CWT of dry matter. The 6R,7R enantiomer is administered in the feed at dietary concentrations of 0.0 or 6.8 g/ton (7.5 ppm) of feed, on a 90% dry matter basis. The cattle are handled under conditions that represent commercial feedlot practices.

Carcass leanness is evaluated using carcass percent protein as the composition variable. Carcass percent protein is the measure of the protein content in the carcass soft tissue which is ultimately merchandised as edible beef. Carcasses with increased levels of protein have a higher percentage of lean meat or red meat yield, and, thus, more merchandisable red meat. The effect of the 6R,7R enantiomer on carcass percent protein analysis is evaluated on a "wet weight" basis (i.e., calculations are not corrected for dry matter content). Additionally, the effects of the 6R,7R enantiomer on carcass percent protein are evaluated on an "equal weight" basis by collecting treated and control carcasses of similar hot carcass weights and quality grades.

Sides of the "equal weight" carcasses are dissected, and the weights are obtained for soft tissues and bone (plus heavy connective tissue or any other inedible tissue such as glands, aorta, etc.). Bone and other inedible tissues are discarded after being weighed. The soft tissue from each carcass is ground, blended, frozen in liquid nitrogen, and powdered. Samples are analyzed for moisture, crude protein, ether extractable lipids, and ash. The average composition of the dissected carcass sides (two per pen) represents the pen's carcass composition for statistical analysis. Change in carcass leanness is measured in differences in percent carcass protein, which is defined as the tissue percent protein times the tissue weight, divided by the carcass weight, times 100.

The words "comprise", "comprises", and "comprising" in this patent (including the claims) are to be interpreted inclusively rather than exclusively. This interpretation is intended to be the same as the interpretation that these words are given under United States patent law.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

We claim:

1. A composition, wherein:
the composition comprises an amount of a 6R,7R enantiomer corresponding in structure to Formula (IA) or a salt thereof:

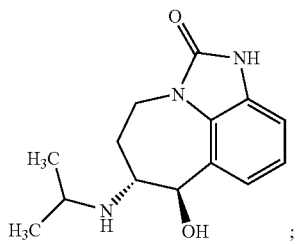

(IA)

and
the amount of the 6R,7R enantiomer or salt thereof in the composition is greater than any amount of any other enantiomer encompassed by Formula (I) or salt thereof:

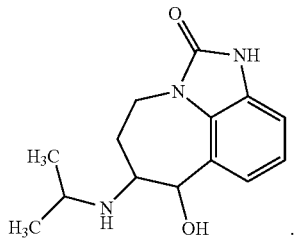

(I)

2. The composition of claim 1, wherein the composition comprises a pharmaceutically acceptable salt of the 6R,7R enantiomer.

3. The composition of claim 1, wherein the composition comprises a food composition.

4. The composition of claim 3, wherein the composition comprises a food composition for poultry.

5. The composition of claim 3, wherein the composition comprises a food composition for fish.

6. The composition of claim 3, wherein the composition comprises a food composition for livestock.

7. The composition of claim 6, wherein the composition comprises a food composition for a bovine animal.

8. The composition of claim 6, wherein the composition comprises a food composition for a swine animal.

9. The composition of claim 1, wherein the ratio of the amount of the 6R,7R enantiomer or salt thereof to the total amount of all other enantiomers of Formula (I) and salts thereof in the composition is greater than about 70:30.

10. The composition of claim 1, wherein the ratio of the amount of the 6R,7R enantiomer or salt thereof to the total amount of all other enantiomers of Formula (I) and salts thereof in the composition is greater than about 95:5.

11. A composition comprising an amount of 6R,7R enantiomer corresponding in structure to Formula (IA) or a salt thereof:

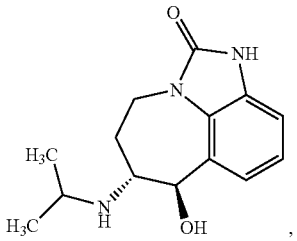

(IA)

wherein the composition exhibits detectably less affinity for μ-opioid receptor binding in vitro than the composition would exhibit if the 6R,7R enantiomer were entirely replaced with racemic trans zilpaterol in an amount that equals twice the amount of the 6R,7R enantiomer.

12. A method for separating enantiomers or salts thereof, wherein the enantiomers correspond in structure to Formula (I):

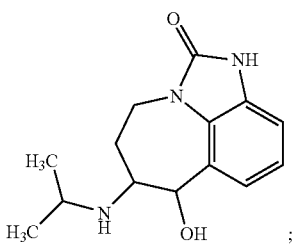

(I)

and
the method comprises forming benzyl carbamates of the enantiomers.

13. The method of claim 12, wherein the benzyl carbamates of the enantiomers are formed by reacting racemic trans zilpaterol with benzyl chloroformate.

14. The method of claim 12, wherein the method further comprises passing the benzyl carbamates of the enantiomers through an HPLC column comprising amylose tris (3,5-dimethylphenylcarbamate) coated on a silica support.

15. A method of feeding an animal, wherein the method comprises feeding the composition of claim 3 to the animal.

16. The method of claim 15, wherein the composition further comprises trenbolone acetate.

17. The method of claim 15, wherein the composition further comprises zeranol or estradiol.

18. A method for increasing an animal's rate of weight gain, wherein the method comprises administering the composition of claim 1 to the animal.

19. A method for improving an animal's feed efficiency, wherein the method comprises administering the composition of claim 1 to the animal.

20. A method for increasing an animal's carcass leanness, wherein the method comprises administering the composition of claim 1 to the animal.

21. The method of claim 18, wherein:
the animal is fed in confinement for slaughter, and
the composition is fed to the animal for from about the last 20 to about the last 40 days that the animal is on feed.

22. A method of increasing beef production, wherein:
the method comprises:
administering a first dosage regimen to a bovine animal for an initial period, and at the end of the initial period, administering a second dosage regimen to the bovine animal for from about 20 to about 40 days;
the first dosage regimen comprises administering an ionophore and an antibiotic in amounts that together constitute a therapeutically effective amount; and
the second dosage regimen comprises administering a composition of claim 1 and essentially no ionophore or antibiotic.

23. A method of reducing feed intake of a bovine animal while maintaining beef production, wherein:
the method comprises:
administering a first dosage regimen to the bovine animal during a finishing period until from about 20 to about 40 days before the end of the finishing period, and during the about 20 to about 40 days before the end of the finishing period,
administering a second dosage regimen to the bovine animal;
the first dosage regimen comprises administering an ionophore and an antibiotic in amounts that together constitute a therapeutically effective amount;
the second dosage regimen comprises administering a composition of a claim 1; and
the composition comprises:
essentially no β-2 agonist other than the enantiomer, and
essentially no ionophore or antibiotic.

24. A method of finishing a bovine animal, wherein:
the method comprises:
administering a first dosage regimen to the bovine animal during a finishing period until from about 20 to about 40 days before the end of the finishing period,
during the about 20 to about 40 days before the end of the finishing period,
administering a second dosage regimen to the bovine animal;
the first dosage regimen comprises administering an ionophore and an antibiotic in amounts that together constitute a therapeutically effective amount;
the second dosage regimen comprises administering a composition of claim 1;
the composition comprises:
essentially no β-2 agonist other than the 6R,7R enantiomer or salt thereof, and
essentially no ionophore or antibiotic; and
the finishing method reduces the risk of a liver abscess in the bovine animal compared to the risk to a similar bovine animal that receives the first dosage regimen throughout the entire finishing period.

25. A method for determining the absolute configuration of an enantiomer corresponding in structure to Formula (I) or a salt thereof:

(I)

wherein the method comprises reacting the enantiomer with 2,4'-dibromoacetophenone to form a 4-bromophenylacetate of the enantiomer.

26. The method of claim 25, wherein the method further comprises analyzing the 4-bromophenylacetate of the enantiomer with x-ray crystallography.

27. The method according to claim 19, wherein:
the animal is fed in confinement for slaughter, and
the composition is fed to the animal for from about the last 20 to about the last 40 days that the animal is on feed.

28. The method according to claim 20, wherein:
the animal is fed in confinement for slaughter, and
the composition is fed to the animal for from about the last 20 to about the last 40 days that the animal is on feed.

* * * * *